United States Patent
Petry

(10) Patent No.: US 6,172,366 B1
(45) Date of Patent: Jan. 9, 2001

(54) DEVICE FOR PRODUCING AND DETECTING INDUCED HEAT RADIATION

(75) Inventor: Harald Petry, Saarbrücken (DE)

(73) Assignee: Phototherm Dr. Petry GmbH (DE)

(*) Notice: Under 35 U.S.C. 154(b), the term of this patent shall be extended for 0 days.

(21) Appl. No.: 09/068,841

(22) PCT Filed: Nov. 7, 1996

(86) PCT No.: PCT/EP96/04869
§ 371 Date: Aug. 21, 1998
§ 102(e) Date: Aug. 21, 1998

(87) PCT Pub. No.: WO97/18459
PCT Pub. Date: May 22, 1997

(30) Foreign Application Priority Data

Nov. 15, 1995 (DE) .............................................. 195 42 534

(51) Int. Cl.[7] .................................................. G01N 21/71
(52) U.S. Cl. ................................. 250/341.6; 250/341.8; 250/347
(58) Field of Search .................... 250/341.6, 341.8, 250/347

(56) References Cited

U.S. PATENT DOCUMENTS

| 3,803,413 | 4/1974 | Vanzetti et al. . |
| 4,745,291 | * 5/1988 | Niiya .............................. 250/559.28 |

OTHER PUBLICATIONS

"Inspection of plasma–sprayed coatings using fast infrared scanning technique", by J. Hartikaninen, Review of Scientific Instruments, 60 (1989) Jul., No. 7, Part 1, New York, USA, pp. 1334–1337.

* cited by examiner

Primary Examiner—Constantine Hannaher
(74) Attorney, Agent, or Firm—Baker & Daniels

(57) ABSTRACT

A device for producing and detecting induced heat radiation, in which movable mirror components are moved into and out of a crossed beam path by a stepping motor so as to be isogonal in the beam path. The stepping motor is controlled in such a manner that when the mirror components enter and leave the beam path, they leave at maximum speed. In another embodiment, a mirror component is pushed into and out of the beam path at a fixed angle of deviation.

13 Claims, 4 Drawing Sheets

DEVICE FOR PRODUCING AND DETECTING INDUCED HEAT RADIATION

BACKGROUND OF THE INVENTION

This invention relates to an apparatus for producing and detecting induced heat radiation with a source of excitation radiation whose output radiation can strike an object, with the heat radiation induced by the source of excitation radiation being detectable by a detector, and with a beam deflector located in the beam path between the source of excitation radiation, the object, and the detector, with the output radiation and the heat radiation proceeding collinearly in a superimposed section between the object and the beam deflector, and with the beam deflector having at least one reflector element connected to a drive unit that limits the superimposed section with the drive unit.

Such a device is disclosed by DE-OS 23 00 436. In this device, there is a tilting mirror inclined with respect to a pulsed and focussed output beam of a laser as the source of excitation radiation, by which on the one hand the output beam can be directed to an object to be examined, and on the other hand, after tilting, infrared radiation collinear with the output beam emitted by the object from the irradiated area can be directed to a detector.

Tests can, in fact, be made with this device on the object with regard to heat dissipation as a reaction to the pulsed, focussed irradiation, but this method is unsuitable for serial tests in industrial quality control because of the necessity of maintaining the tilt angle precisely relative to the output beam, on the one hand, and on the other hand relative to the detector, and the resultant susceptibility to errors. Furthermore, additional devices have to be provided to keep the output beam away from the moving mirror when detecting the infrared radiation to prevent irradiation of the highly sensitive detector with stray scattered radiation. It is also a result of the tipping process that the end positions with the precise angles to be reached can be firmly assumed only after a relatively long period of time.

A device for separating and recombining optical radiation is disclosed by DE-PS 12 91 533, in which precisely reproducible dark pauses of equal length can be produced in two arms with a comparison substance and a test substance independently of the radiation path length, by means of rotating reflector disks with reflective, absorbing, and transparent sectors that have different sector angles. Certain tolerances are permissible here in the relative phase of the reflector disks and the congruence between the beam cross sections in the separating and combining regions, without giving rise to erroneous measurements.

A method and a device for controlling the production of welded seams are disclosed by GB 1 484 181, in which infrared radiation emitted from the two sides of the applied welded seam is directed in two focused beams to a detector by a sector wheel with reflective and perforated sectors. This is intended for reliable monitoring of the quality of the welded seam.

DE 40 15 893 A1 discloses a device for contactless and nondestructive examination of the internal and/or external structure of absorbing test specimens, in which induced temperature modulation can be produced locally with an intensity-modulated excitation beam. The back-emitted infrared radiation is separable from the excitation radiation by passing through a dichroic beam splitter that is also impacted by the excitation beam, and is diverted to a detector. It can in fact be determined with this device whether detected effects come from the interior or the surface of the material, but there is a high proportion of scattered light especially when evaluating close to the wavelength of the excitation radiation, which is detrimental to the signal/noise ratio and prevents measurements of weak signals.

DE 43 43 076 A1 discloses a device for the photothermal testing of a surface, in which excitation radiation falls on a surface to be tested through an opening in a focusing lens. The back-emitted heat radiation is fed to a detector through the focusing lens. Because of the separation of excitation radiation and heat radiation with no common optical elements, the individual components can be matched optimally to the individual wavelengths and in particular, back-emitted heat radiation can be evaluated even in the spectral region close to the excitation radiation without optical elements impacted by both radiations leading to superimposition of the measured signal and the excitation radiation, in which case either the excitation radiation would strike the detector with substantial intensity or the heat radiation would be prevented from reaching the detector. This device, however, has the drawback that the sizes of the optical elements have to be matched precisely to one another for a given beam geometry to produce minimal losses through the opening in the focusing lens.

The underlying purpose of this invention is to provide a device of the type mentioned initially that is stable in its optical precision in fast serial tests and is not susceptible to problems.

SUMMARY OF THE INVENTION

This problem is solved pursuant to the invention by providing that at least one reflecting element can be introduced completely into the beam path and removed completely from the beam path, and has a fixed angle of deflection with respect to the superimposed section.

Because of introduction at the proper angle and complete removal of the reflector from the beam path, on the one hand, a high rate is achieved during the alternation between impacting the object with output radiation and detection of the heat radiation, and on the other hand, high optical accuracy of collinearity is achieved between the output radiation of the excitation radiation source and the heat radiation, so that there is high spacing tolerance. Furthermore, because of the proper angular introduction into the beam path and removal of the reflector from the beam path, easily controlled deflection and absorption of the output beam can be accomplished. Low positioning precision is sufficient for the reflector with respect to the beam path during introduction and removal.

In a desirable embodiment, at least two reflecting elements, for example with circular segmental, circular, or oval shape, are attached to a rotating axle of a stepping motor and can be rotated into the beam path for the reflection position and out of the beam path for the transmission position with a fixed angle of deflection for the radiations. In another embodiment, one reflecting element can be shifted into the beam path and out of the beam path with a fixed angle of deflection.

It can be provided in both embodiments that either the output radiation or the heat radiation is reflected. It is especially desirable for the particular reflecting element to enter and to leave the beam path at high speed, so that any undesirable nonuniform irradiation of the object and only partial impacting of the detector with heat radiation, and any overlapping of the irradiation and emission phases, are minimized. This can be accomplished with technical ease both when rotating in and rotating out, or shifting in and shifting out, by providing that the reflecting elements are accelerated prior to ending the reflection when impacted with the radiation in question, so that the interruption of irradiation or pause in measurement is minimized before switching into the transmission position.

BRIEF DESCRIPTION OF THE DRAWINGS

Other desirable refinements and advantages of the invention are found in the following description of examples of embodiment, with reference to the accompanying drawings wherein.

DESCRIPTION OF THE PREFERRED EMBODIMENT

Figure 1:
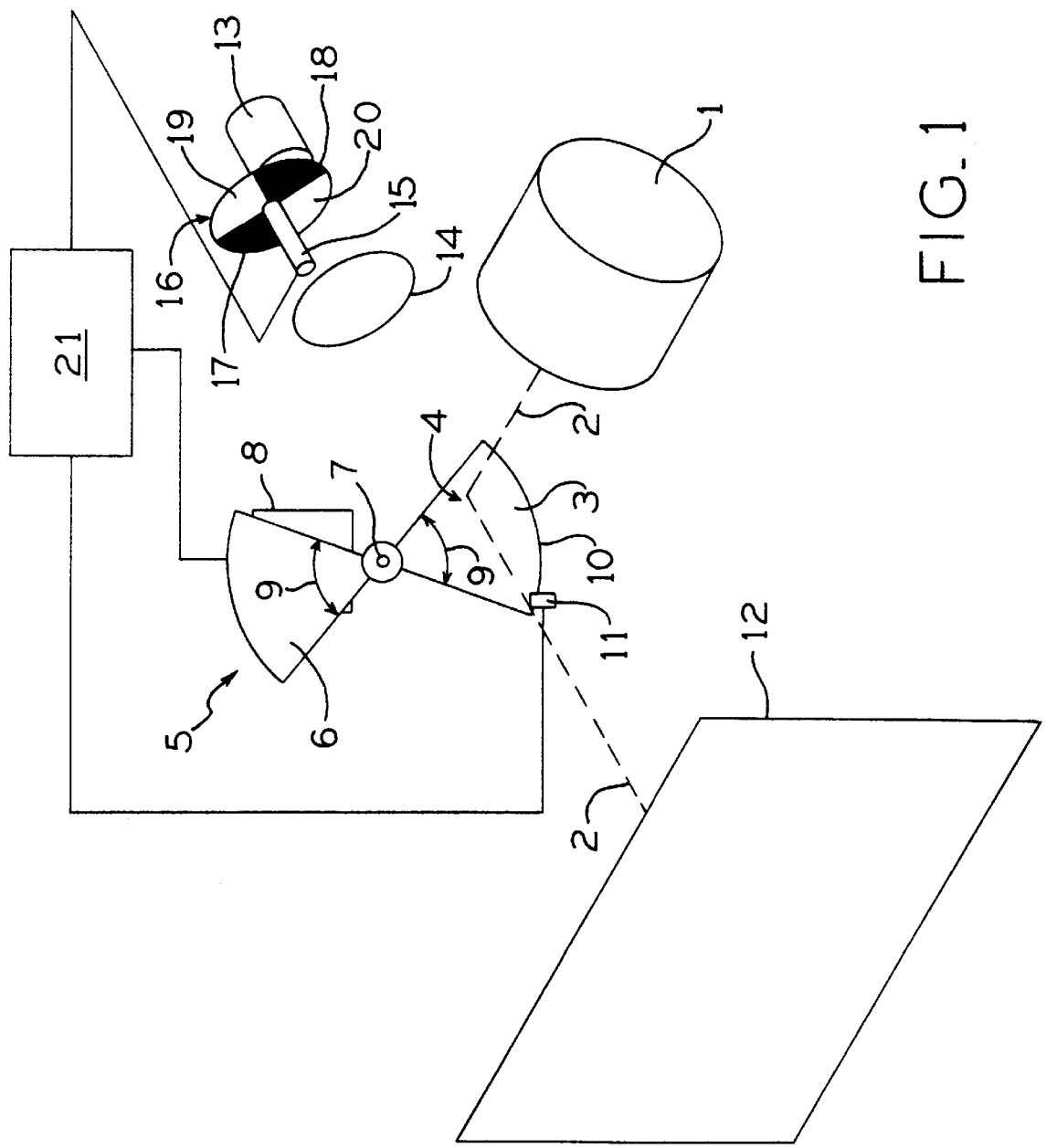
FIG. 1 is a schematic view of a device for producing and detecting induced heat radiation with two reflection elements that can be rotated into and out of the beam path, in which one reflecting element is impacted by output radiation from an excitation radiation source, to produce induced heat radiation.

FIG. 1 shows schematically the basic structure of an example of embodiment of a device for producing and detecting induced heat radiation pursuant to the invention. The device of FIG. 1 has a continuously radiating light source 1 as a broad-band excitation radiation source, for example a halogen lamp with a few tens of watts of power consumption, with which, after passing through beam-shaping optics and shielding diaphragms not shown in FIG. 1, a slightly divergent broad-band output beam 2 can be produced with a divergence angle of a few degrees.

In the reflection position shown in FIG. 1, the output beam 2 impacts the edge area 4 of a reflecting element 3 slanted from the output beam 2 in the form of a circular segment. The reflecting element 3 is part of a beam-diverting device 5 that has another circular segmental reflecting element 6 that is opposite the aforementioned reflecting element 3 and in the same reflecting plane. The reflecting elements 3, 6 are attached to a rotating axle 7 of a stepping motor 8, shown partly covered in the illustration of FIG. 1, by which the reflecting elements 3, 6 can be rotated with identical fixed angles of deflection. Each of the reflecting elements 3, 6 has a segment angle 9 that is at most half of the full angle of 360 degrees divided by the number of reflecting elements 3, 6. The positions of the reflecting elements 3, 6 are detectable by a fixed angular photodetector 11 placed on the outer edge 10 of a reflecting element 3, 6, as a position detector.

After reflection on the reflecting element 3, the output beam 2, strikes an object 12, on which the thickness of a coating applied to the surface, particularly a coating of paint, is to be determined, for example.

The device shown in FIG. 1 also has a detector 13 that is highly sensitive in the spectral region for heat radiation at room temperature, with which, as will be explained in detail later, the decay of the heat radiation induced by the output beam 2 can be detected through focusing optics 14. The detector 13 has a spectral sensitivity characteristic that matches the spectrum of the induced heat radiation for maximum signal output in this example of embodiment at room temperature, or in modifications also at higher or lower characteristic temperature of the object 12. Because of this, a relatively low-intensity light source 1 is sufficient to obtain satisfactory measurement signals.

There is a shielding or screening disk 16 that can be rotated by a shield disk drive 15, just in front of the input window of the detector 13. The shielding disk 16 has two opposite shielding segments 17, 18 that are opaque in the spectral region of the output beam 2, and two transmission segments 19, 20 that are transparent at least for the heat radiation. In the position of the screening disk 16 shown in FIG. 1, the screening segment 18 is rotated in front of the input window of the detector 13 to protect the highly sensitive detector 13 against overloading or even destruction from stray radiation from the white light source 1 that may be very much more intense than the heat radiation to be detected.

There is also an electronic rotation-control unit 21 to which the stepping motor 8, the angular photodetector 11, and the screening disk drive 15 are connected.

Figure 2:
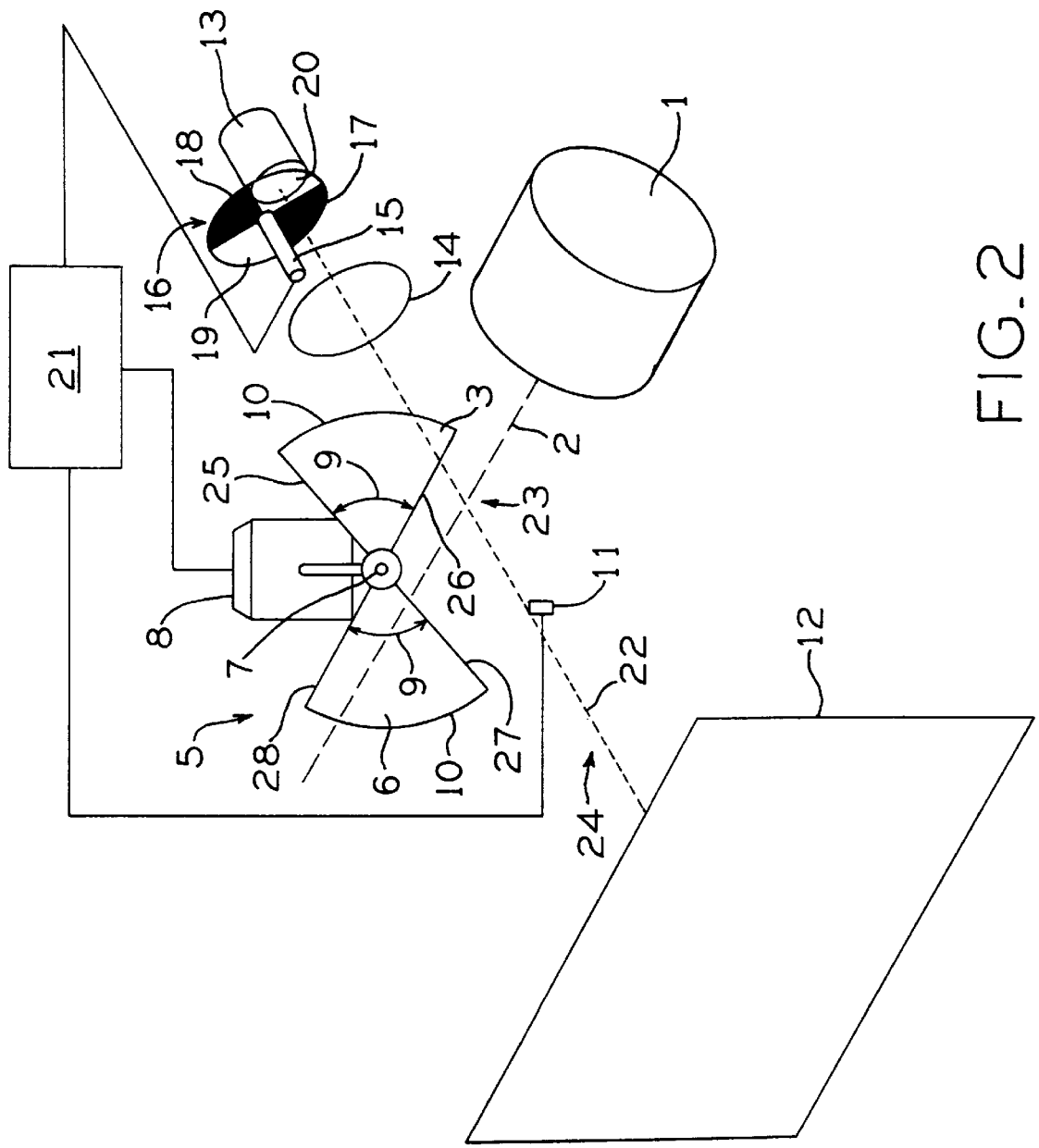
FIG. 2 is a schematic view of the device pursuant to FIG. 1 with reflecting elements rotated out of the beam path to detect the induced heat radiation with a detector.

FIG. 2 shows the device pursuant to FIG. 1 with the reflecting element 3, which is rotated by control signals from the rotation-control unit 21 out of the beam path 23 formed by the output beam 2 and a thermal beam 22 produced during and after irradiation with the output beam 2 by thermooptical processes on the surface of the object 12. After the reflecting element 3 is rotated out of the beam path 23 into the transmission position, the output beam 2 crosses the heat beam 22 at essentially a right angle in the arrangement according to FIGS. 1 and 2, and is absorbed, for example, in an absorber not shown in FIGS. 1 and 2. In the device shown in FIGS. 1 and 2, the output beam 2 and the heat beam 22 are collinear with one another between the reflection in the edge area 4 of the reflecting elements 3, 6 and the object, in a superimposed section 24, which guarantees that measurement is largely independent of spacing.

In the transmission position of the reflecting elements 3, 6 shown in FIG. 2, the screening disk 16 is also in a position in which the transmission segment 20 is rotated by control signals from the rotation-control unit 21 to be in front of the input window of the detector 13 so that the heat beam 22 strikes the detector 13. Besides broad-band energy utilization of the white light source 1, the broad band also provides relatively high spectral independence from the color composition of the materials of the object 12 producing the heat radiation.

To obtain reliable measured data when determining the thickness of a coating applied to the surface of the object 12, the stepping motor 8 is controlled by the rotation-control unit 21 by signals with increasing frequency, so that the reflecting element 3 has reached a maximum speed when rotating out of the beam path 23 along the largest possible angular acceleration distance between the edge area 4 located close to a leading edge 25 impacted by the output beam 2 and a trailing edge 26 of the reflecting element 3 opposite the leading edge 25. The beam path 23 is traversed typically in a few milliseconds. This assures that there is only a very brief nonuniform illumination of the object 12 and only a very brief partial impacting of the detector 13 by the heat beam 22, and only brief overlapping of irradiation and emission phases, with only correspondingly insignificant effect on the measured data when measuring the decay of intensity of the heat beam 22, in particular also with short measurement times of a few milliseconds.

After the reflecting element 3 has rotated out of the beam path 23, the stepping motor 8 is braked by control signals of decreasing frequency from the rotation-control unit 21, and is rotated into a central position for unhindered passage of the output beam 2 and of the heat beam 22 between the reflecting elements 3, 6. In a modification, the rotating axle 7 is slowly rotated further without hindrance to the passage of the heat beam 22 between the reflecting elements 3, 6 during the transmission phase.

To begin a new measurement, the stepping motor 8 is again accelerated, with a leading edge 27 of the other reflecting element 6 this time traversing the output beam 2 in the same direction of rotation at maximum speed. After braking the stepping motor 8 with continuous reflection of the output beam 2 at the reflecting element 6 before reaching a trailing edge 28 opposite the leading edge 27, the reflecting element 6 is rotated by control signals from the rotation-control unit 21 in such a way that the output beam 2 impacts the reflecting element 6 corresponding to the arrangement shown in FIG. 1 in an edge area 4 adjacent to the leading edge 27.

Just before the reflecting element 6 is rotated in, the screening disk 16 is rotated by control signals from the rotation-control unit 21 far enough for the shielding segment 17 to protectively cover the detector 13. The angular photodetector 11 detects the passage of a leading edge 25, 27, so that on the one hand the position of the rotating axle 7 of the stepping motor 8 can be detected, and on the other hand, the number of control signals from the rotation-control unit 21 can be corrected so that any rotational dislocations can be compensated for.

The design described above on the one hand provides spacing-independent irradiation of the object 12 by the rotating reflecting elements 3, 6 positioned in a plane, with fixed angle of deflection from the collinear orientation of the output beam 2 and the heat beam 22 in the superimposed section 24, and on the other hand, it precludes mixing of beam fractions of the same frequency ranges of the output beam 2 with the heat beam 22 because of the timed beam separation, so that even heat radiation in a frequency range in which there is also intense emission from the broad-band light source, for example the white light source 1, can be fed to the detector 13.

Figure 3:
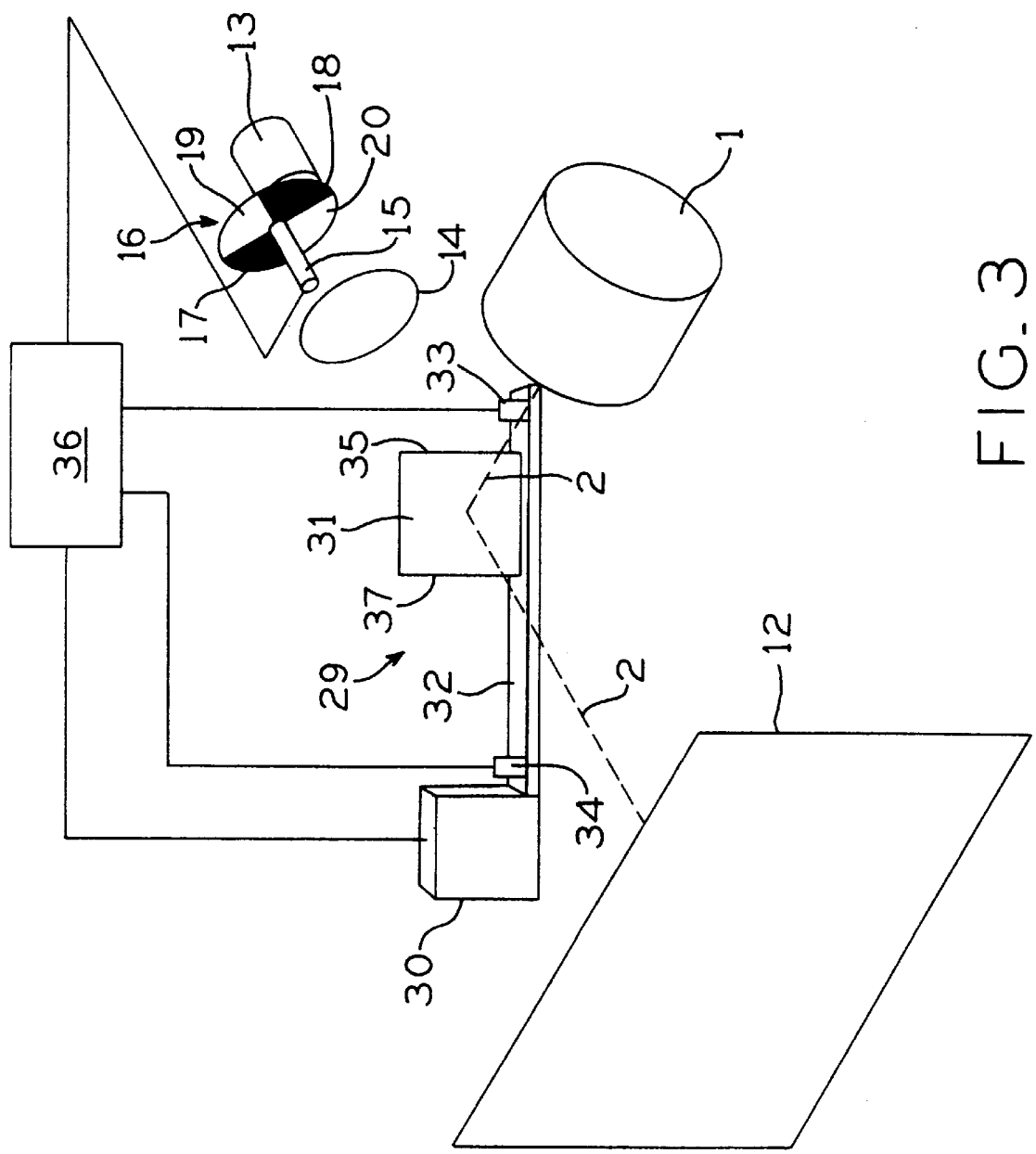
FIG. 3 is a schematic view of another embodiment of a device for producing and detecting induced heat radiation with a reflecting element that can be shifted into and out of the beam path, in a position in which it is impacted by output radiation from an excitation radiation source to produce the induced heat radiation.

FIG. 3 shows in perspective the basic structure of another example of embodiment of a device for producing and detecting induced heat radiation according to the invention. In the device according to FIG. 3, the parts of the device are assigned reference symbols to correspond to the device of FIGS. 1 and 2 and are not further explained in detail. The device according to FIG. 3 has a translation beam deflector 29 as the beam deflector, that has a translation reflector 31 driven by a translation motor 30. The translation reflector 31 can be shifted on a running rail 32 at a fixed angle of deflection relative to the output beam 2, between a reflection position and a transmission position, with the output beam 2 of the white light source 1 being reflected to the object 12 in the reflection position that is almost assumed in the position of the translation reflector 31 according to FIG. 3.

The two positions of the translation reflector 31 are detectable by means of a reflection photodetector 33 and a transmission photodetector 34 as position detectors, with the reflection photodetector 33 and the transmission photodetector 34 being attached to the ends of the running rail 32. In the position of the translation reflector 31 shown in FIG. 3, the end position for reflection is almost reached, inasmuch as a beam edge 35 of the transmission reflector 31 facing toward the output beam 2 has traversed the output beam 2. In the reflection position of the translation reflector 31, a signal emitted by the reflection photodetector 33 can be input to a translation control unit 36, with which the shifting controlled by the translation control unit 36 can then be braked by the translation motor 30 connected to it, and comes to a stop with a reflection close to a reflection end 37 of the translation reflector 31 opposite the beam edge 35.

In this reflection position, the detector 13 is protected against overload by the shielding disk 16 that can be rotated by control signals from the translation control unit 36, with shielding segment 18 in front.

Figure 4:
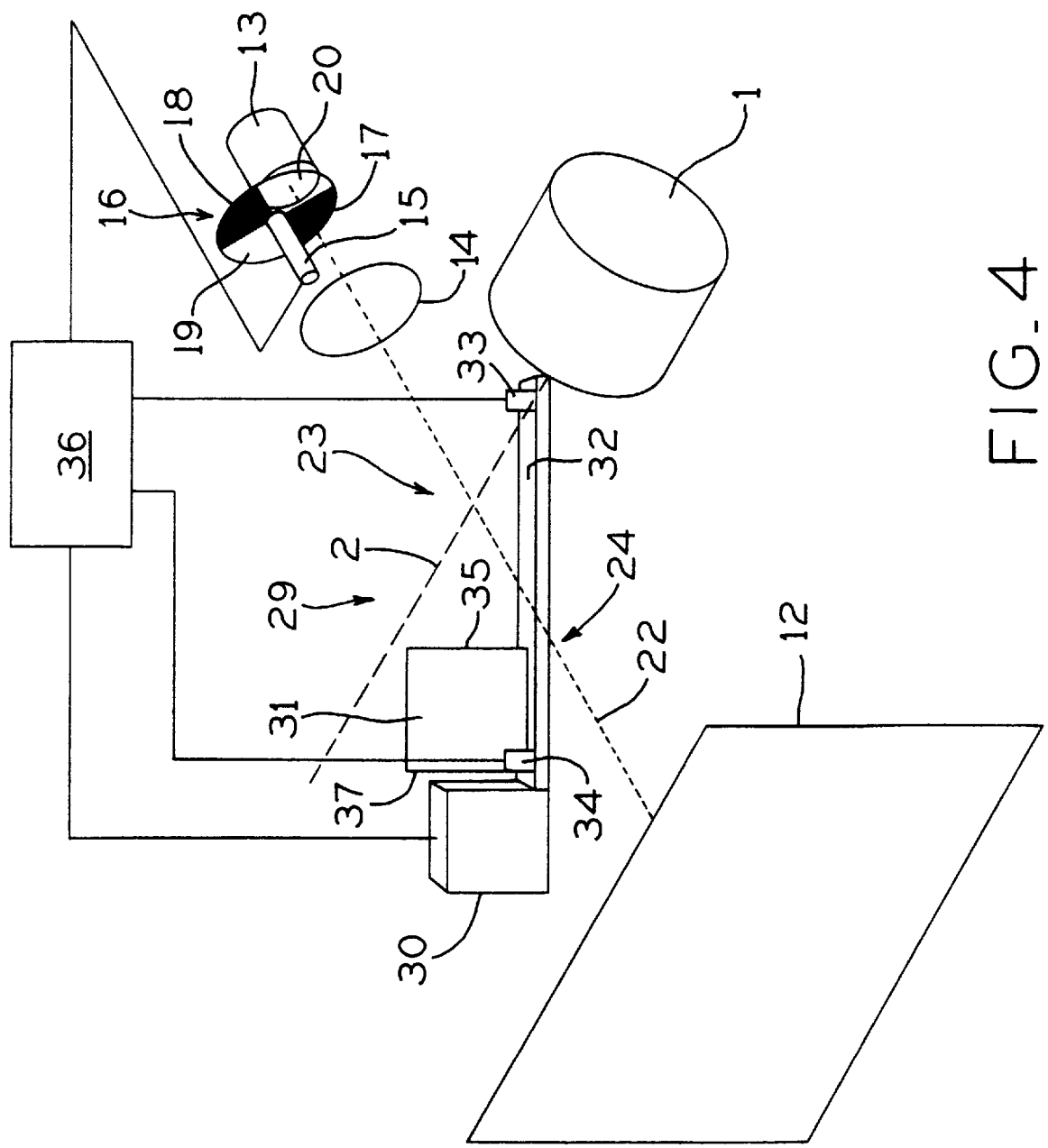
FIG. 4 is a schematic view of the device pursuant to FIG. 3 with the reflecting element shifted out of the beam path to detect the induced heat radiation with a detector.

FIG. 4 shows the device according to FIG. 3 with the translation reflector 31 shifted into the transmission position after sufficient irradiation of the object 12 by the output beam 2. A portion of the heat radiation then passes by the translation reflector 31 shifted out of the beam path 23, and as a heat beam 22 through the focusing optics 14 and through the transmission segment 20 of the shielding disk 16 after it is rotated to the front, it reaches the detector 13 for measurement, whose output signal can be fed to the translation control unit 36 to evaluate the intensity of the heat beam 22 decaying with time.

The shifting of the translation reflector 31 by the translation control unit 36 in the example of embodiment shown in FIGS. 3 and 4 also occurs in such a way that the beam edge 35 cuts through the output beam 2 at a maximum speed, typically within a few milliseconds, so that in this case also the measurement errors resulting from nonuniform irradiation of the object 12 and only partial transmission of the heat beam 22, and from overlapping of the irradiation and emission phases, are minimized. The collinear orientation of the output beam 2 and the heat beam 22 for the necessary spacing independence is likewise achieved by the shifting of the translation reflector 31 at a fixed angle of deflection.

In forms of embodiment modified from the examples of embodiment according to FIGS. 1, 2, 3, and 4, the positions of the white light source 1 and of the detector 13 preceded by focusing optics 14 and shielding disk 16 are interchanged, so that the output beam 2 strikes the object 12 in the transmission positions, and the heat beam 22 is reflected to the detector 13 in the reflection positions.

What is claimed is:

1. An apparatus for producing and detecting induced heat radiation comprising a source of excitation radiation for generating output radiation along a beam path whereby said output radiation can strike an object, a detector for detecting heat radiation induced in the object by the source of excitation radiation, a beam deflector disposed in the beam path between the source of excitation radiation and the object, and between the object and the detector, the output radiation and the heat radiation proceeding collinearly in a superimposed section of the beam path between the object and the beam deflector, said beam deflector including a reflector element connected to a drive element for diverting said output radiation from the source of excitation radiation to the object, said reflector element completely introduceable into the beam path and completely removable from the beam path, said reflector element disposed at a fixed angle of deflection relative to said superimposed section.

2. An apparatus according to claim 1, including a position detector and wherein the position of said reflector element can be determined by said position detector.

3. An apparatus according to claim 1 wherein said reflector element moves at its maximum achievable speed when entering the beam path and when leaving the beam path.

4. An apparatus according to claim 3, wherein the reflector element is positionable by the drive element into a position in which it can be impacted by one of the output radiation of the excitation radiation source and the heat radiation in an edge area located in front in the direction of motion outside of the beam path, so that during removal of the reflector element out of the beam path, the reflector element is impacted by the radiation over a maximum acceleration path.

5. An apparatus according to claim 4, wherein the spectral sensitivity of the detector matches the spectral intensity distribution of the heat radiation with respect to maximum signal output.

6. An apparatus according to claim 1, wherein the drive element has a stepping motor with a rotating axle to which said reflector element is attached, said reflector element rotatable into the beam path and out of the beam path.

7. An apparatus according to claim 6, wherein the beam deflector has two opposed reflector elements.

8. An apparatus according to claim 7, wherein each reflector element has a circular segment shape with a segmental angle.

9. An apparatus according to claim 8, wherein the segmental angle of each reflector element corresponds at most to half of the full angle of 360 degrees divided by the number of reflector elements.

10. An apparatus according to claim 1, wherein the drive element has a translation element whereby said reflector element can be shifted into the beam path and out of the beam path.

11. An apparatus according to claim 10, including two position detectors for detecting the end position of the reflector element.

12. An apparatus according to claim 1, wherein the excitation radiation source is a broad-band light source.

13. An apparatus for producing and detecting induced heat radiation comprising a source of excitation radiation for generating output radiation along a beam path whereby said output radiation can strike an object, a detector for detecting heat radiation induced in the object by the source of excitation radiation, a beam deflector disposed in the beam path between the source of excitation radiation and the object, and between the object and the detector, the output radiation and the heat radiation proceeding collinearly in a superimposed section of the beam path between the object and the beam deflector, said beam deflector including a reflector element connected to a drive element for diverting said heat radiation from the object to said detector, said reflector element completely introduceable into the beam path and completely removable from the beam path, said reflector element disposed at a fixed angle of deflection relative to said superimposed section.

* * * * *